(12) United States Patent
Hironaka (10) Patent No.: US 9,651,510 B2
(45) Date of Patent: May 16, 2017

(54) VOLTAGE MEASURING APPARATUS WITH TEMPERATURE ABNORMALITY DETECTION FUNCTION AND POWER CONVERSION APPARATUS

(71) Applicant: Ryouji Hironaka, Gamagori (JP)

(72) Inventor: Ryouji Hironaka, Gamagori (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 14/764,399

(22) PCT Filed: Jan. 24, 2014

(86) PCT No.: PCT/IB2014/000179
§ 371 (c)(1),
(2) Date: Jul. 29, 2015

(87) PCT Pub. No.: WO2014/118625
PCT Pub. Date: Aug. 7, 2014

(65) Prior Publication Data
US 2015/0377808 A1  Dec. 31, 2015

(30) Foreign Application Priority Data
Feb. 1, 2013  (JP) .................................. 2013-018454

(51) Int. Cl.
| H02P 1/00 | (2006.01) |
|---|---|
| G01N 25/72 | (2006.01) |
| H02M 1/32 | (2007.01) |
| G01K 3/00 | (2006.01) |
| G01K 7/22 | (2006.01) |

(Continued)

(52) U.S. Cl.
CPC ............. *G01N 25/72* (2013.01); *G01K 3/005* (2013.01); *G01K 7/22* (2013.01); *H02H 7/1216* (2013.01); *H02M 1/32* (2013.01); *H02M 7/537* (2013.01); *H02P 27/06* (2013.01); *G01K 2205/00* (2013.01); *H02M 2001/327* (2013.01)

(58) Field of Classification Search
CPC ........................... H02K 7/20209; H02H 6/005
USPC .................................................. 318/139, 471
See application file for complete search history.

(56) References Cited

U.S. PATENT DOCUMENTS

| 6,078,511 A | 6/2000 | Fasullo et al. |
| 2004/0174720 A1* | 9/2004 | Kurokami ......... H02M 7/53871 363/16 |

(Continued)

FOREIGN PATENT DOCUMENTS

| JP | 03-004274 U | 1/1991 |
| JP | 05-006826 U | 1/1993 |

(Continued)

*Primary Examiner* — Rina Duda
(74) *Attorney, Agent, or Firm* — Sughrue Mion, PLLC (57) ABSTRACT

A voltage measuring apparatus is configured to measure voltage between a positive terminal and a negative terminal of a device, and the voltage measuring apparatus includes: a PTC thermistor that is connected to one of terminals of the device; and a measuring circuit that measures voltage of one of the terminals through the PTC thermistor with respect to a specified reference potential and voltage of the other of the terminals with respect to the reference potential. The voltage measuring apparatus detects temperature abnormality of the device or components associated with the device.

6 Claims, 5 Drawing Sheets

(51) Int. Cl.
*H02H 7/12* (2006.01)
*H02M 7/537* (2006.01)
*H02P 27/06* (2006.01)

(56) References Cited

U.S. PATENT DOCUMENTS

| | | | | |
|---|---|---|---|---|
| 2009/0315396 | A1* | 12/2009 | Ichikawa | B60L 3/0046 307/24 |
| 2011/0241581 | A1* | 10/2011 | Flock | B60L 3/04 318/400.3 |
| 2012/0019176 | A1* | 1/2012 | Okamura | B60K 6/445 318/376 |
| 2013/0027827 | A1 | 1/2013 | Ge et al. | |

FOREIGN PATENT DOCUMENTS

| | | | |
|---|---|---|---|
| JP | 2008312398 A | 12/2008 | |
| JP | 2009-111370 A | 5/2009 | |

* cited by examiner

| TARGET VOLTAGE (= 500V) | | POSITIVE ELECTRODE SIDE | | NEGATIVE ELECTRODE SIDE | |
| --- | --- | --- | --- | --- | --- |
| | | POTENTIAL OF POSITIVE OUTPUT PORT P1 | MEASUREMENT VOLTAGE | POTENTIAL OF NEGATIVE OUTPUT PORT P2 | MEASUREMENT VOLTAGE |
| CASE 1 | 500V OUTPUT (NORMAL OUTPUT) | 250V | 1.25V | -250V | -1.25V |
| CASE 2 | 300V OUTPUT (CONVERTER ABNORMALITY) | 150V | 0.75V | -150V | -0.75V |
| CASE 3 | 500V OUTPUT (TEMPERATURE ABNORMALITY) | 250V | 1.25V | -250V | -0.01V |

FIG. 5

VOLTAGE MEASURING APPARATUS WITH TEMPERATURE ABNORMALITY DETECTION FUNCTION AND POWER CONVERSION APPARATUS

BACKGROUND OF THE INVENTION

1. Field of the Invention

The present invention relates to a voltage measuring apparatus and a power conversion apparatus for an electric vehicle that uses the voltage measuring apparatus.

2. Description of Related Art

Electronic equipment that includes elements generating a large amount of heat is often subjected to temperature measurement of the elements. When the temperature exceeds a specified threshold, some kind of process such as generation of an alarm or limitations on electric power flowing to the electronic equipment is frequently executed in the electronic equipment. Hereinafter, the detection in which the temperature of the element exceeds the specified threshold is referred to as a "temperature abnormality detection".

One of the devices that generate a large amount of heat is a power conversion apparatus that is equipped in the electric vehicle. The power conversion apparatus in the electric vehicle converts electric power of a battery into alternating-current (AC) power for driving a drive motor. Such an element in the power conversion apparatus handles a large amount of electric power and thus generates a large amount of heat. In particular, switching elements in a voltage converter or an inverter and a capacitor for smoothing output current of the battery or the voltage converter generates a large amount of heat, and their heat resistant temperatures are low. Then, when the temperature of the capacitor exceeds the specified threshold (that is, the temperature abnormality of the capacitor is detected), some kind of process is executed.

A thermistor is often used for the temperature abnormality detection of the capacitor. The thermistor is a resistor in which the resistance sharply changes when its temperature exceeds a predetermined temperature. That is to say, the temperature abnormality in adjacent areas of the thermistor can be detected, based on the resistance of the thermistor. Techniques for the temperature abnormality detection by means of the thermistor are disclosed in Japanese Patent Application Publication No. 2009-111370 (JP 2009-111370 A) and Japanese Utility Model Application Publication No. 03-4274 (JP 03-4274 U), for example.

SUMMARY OF THE INVENTION

When the temperature abnormality is detected by means of the thermistor, it is required that the thermistor is mounted on a detection location of the temperature abnormality and the thermistor is connected to a detection circuit for the temperature abnormality with two cables. Thus, two dedicated cables are required to be routed for the temperature abnormality detection, and a dedicated temperature abnormality detection circuit is required to be provided. The object of the present invention is to provide a voltage measuring apparatus and a power conversion apparatus using the voltage measuring apparatus that can improve the efficiency of routing of the cables in the electronic equipment by sharing the cable for the temperature abnormality detection with other cables for other purposes and also can share the circuit for the temperature abnormality detection with other circuits for other purposes.

In the temperature abnormality detection by means of the thermistor, the abnormality is detected by comparing the voltage of the thermistor with the specified threshold. On the other hand, some electronic equipment may measure the voltage between the terminals of a particular device. In other words, the voltage measuring apparatus may be incorporated into the electronic equipment. The technique disclosed herein incorporates a temperature abnormality detection function into the apparatus that measures the voltage of the particular device in the electronic equipment. That is to say, the present invention provides a voltage measuring apparatus with the temperature abnormality detection function. The voltage measuring apparatus according to a first aspect of the present invention is configured to measure voltage between a positive terminal and a negative terminal of a device, and the voltage measuring apparatus includes: a positive temperature coefficient (PTC) thermistor that is connected to one of terminals of the device; and a measuring circuit that measures voltage of one of the terminals through the PTC thermistor with respect to a specified reference potential and voltage of the other of the terminals with respect to the reference potential. The voltage measuring apparatus detects temperature abnormality of the device or components associated with the device. The PTC thermistor may be mounted on a location where the temperature abnormality is detected. The PTC thermistor is a thermistor whose resistance sharply increases at the specified temperature referred to as a Curie point temperature or higher. The resistance at the Curie point temperature or lower is extremely smaller than the maximum resistance during the temperature rise. Thus, an influence, on the accuracy of the voltage measurement is small at the Curie point temperature or lower. Hereinafter, the PTC thermistor may simply be referred to as the "thermistor" in some cases.

A general voltage measuring apparatus is connected to two terminals of the device by means of two cables. However, in the voltage measuring apparatus disclosed herein, the thermistor is connected in series between one of the terminals of the device and one of input ports of the voltage measuring apparatus. The thermistor is mounted on the location where the temperature abnormality is detected. This apparatus can be connected to the device with two cables and can measure the voltage between the terminals of the device and detect the temperature abnormality. In other words, two dedicated cables to the temperature abnormality detection are not required to be routed.

When the thermistor is simply connected in series to the cable between the device and the conventional voltage measuring apparatus, the determination cannot be made whether the measured voltage indicates the true output voltage of the device or unexpectedly indicates the result of an increase in the resistance of the thermistor due to the temperature abnormality. Therefore, the technique disclosed herein employs an unique measuring circuit. The measuring circuit measures the voltage of one of the terminals through the thermistor with respect to the specified reference potential and the voltage of the other of the terminals with respect to the reference potential. Hereinafter, a process for detecting the temperature abnormality based on the two measured voltage values is described with specific examples.

In the aspect described above, the device may be the voltage converter that converts the output voltage of the battery and maintains the positive output port at higher potential than the reference potential and the negative output port at lower potential than the reference potential. Such a voltage converter is incorporated into the power conversion apparatus for the electric vehicle that converts output power of the battery into alternating-current power for driving the drive motor. The drive motor operates on the alternating-current power that possesses the reference potential as zero potential and alternates between a positive potential and a negative potential with a specified voltage width. Thus, the electric power of the battery is converted into the voltage that possesses the positive and the negative potentials with respect to the reference voltage as zero with the voltage converter disposed in a front stage of the inverter. The reference potential is generally referred to as the ground potential. In the case of the electric vehicle, the reference potential corresponds to the potential of the body ground.

In the aspect described above, the voltage measuring apparatus may detect the temperature abnormality of the device or the components associated with the device based on the voltage of one of the terminals and the voltage of the other of the terminals. Furthermore, the measuring circuit may output a signal that indicates the temperature abnormality detection when an absolute value of the voltage of one of the terminals through the PTC thermistor is different from an absolute value of the voltage of the other of the terminals. The voltage converter for the electric vehicle described above maintains the positive output port at higher potential than the reference potential by half of target voltage (target output voltage) and the negative output port at lower potential than the reference potential by the remaining half of the target voltage. Subsequently, the voltage that is output by the voltage converter (that is, the difference between the potential of the positive output port and the potential of the negative output port) becomes the target voltage. Thus, the voltage converter has a relation such that the absolute value of the voltage of the positive output port with respect to the reference potential is equal to the absolute value of the voltage of the negative output port with respect to the reference potential. Even if the output voltage of the voltage converter does not reach the target voltage, the relation described above is maintained. Thus, when the relation described above is not established, the resistance of the thermistor increases, and consequently, the occurrence of the temperature abnormality can be determined. In this case, the signal that indicates the occurrence of the temperature abnormality is output. In contrast, when the relation described above is established, it is expected that the resistance of the thermistor is small, that is, the temperature abnormality does not occur, and thus the difference between two measured voltages is output as the voltage between the output terminals of the device (that is, the output voltage of the voltage converter). Consequently, the usual voltage measurement between the output ports can be executed, and the temperature abnormality at the location where the thermistor is disposed can be detected. The measured temperature has some variations, and thus the voltage converter outputs the signal indicating the occurrence of the temperature abnormality in practice when the difference between the absolute value of the voltage of the positive electrode with respect to the reference potential and the absolute value of the voltage of the negative electrode with respect to the reference potential exceeds a specified range corresponding to the variations. When the temperature abnormality is detected, some kind of process needs to be provided to the device on which the temperature abnormality occurs even if the voltage converter normally operates in the first place, and thus the true output voltage of the voltage converter may not be measured.

The relation in which the absolute value of the voltage of the positive output port with respect to the reference potential is equal to the absolute value of the voltage of the negative output port with respect to the reference potential is not established even when the positive output port or the negative output port becomes shorted with the ground. However, the electric vehicle is generally equipped with a short-circuit detector, and thus the short circuit can be detected with the short-circuit detector when the relation described above is not established due to the short circuit. The controller of the electric vehicle determines that the resistance of the thermistor increases (that is, the temperature abnormality occurs) when the relation described above is not established and the short-circuit detector does not detect the short circuit.

In the aspect described above, the device may be the inverter that supplies alternating-current power to the drive motor for the electric vehicle, the voltage measuring apparatus may be connected to direct-current input ports of the inverter, one terminal in the direct-current input ports of the inverter may be maintained at higher potential than the reference potential, and the other terminal in the direct-current input ports may be maintained at lower potential than the reference potential. Thus, the input port of the inverter has the relation described above, that is, the absolute value of the voltage of one of the input ports with respect to the reference potential is equal to the absolute value of the voltage of the other of the input ports with respect to the reference potential. Therefore, the detection of the increase in the resistance of the thermistor described above can be achieved.

In the aspect described above, the PTC thermistor may be mounted on the capacitor that is connected between the terminals of the device. In other words, the subject of the temperature abnormality detection may typically be the capacitor that is connected between the terminals of the device (voltage converter or inverter). The voltage measuring apparatus may be incorporated into the power conversion apparatus for the electric vehicle that converts output power of the battery into the alternating-current power for driving the drive motor. The structure that is unique to the power conversion apparatus for the electric vehicle (the structure such that the input port of the inverter or the output port of the voltage converter disposed in the front stage of the inverter is maintained at the positive or the negative potential that possesses the reference potential as zero) is used to eliminate the need of the cables dedicated to the temperature abnormality detection. The voltage measuring apparatus functions as the circuit that detects the temperature abnormality.

A power conversion apparatus according to a second aspect of the present invention is configured to boost electric power of a battery and then convert it into alternating-current power for driving a drive motor, and the power conversion apparatus includes: a voltage converter that boosts output voltage of the battery and maintains a positive output port at higher potential than reference potential corresponding to zero potential of the alternating-current power and a negative output port at lower potential than the reference potential; a capacitor that is connected between the output ports of the voltage converter; a PTC thermistor that is mounted on the capacitor and connected to one of the output ports of the voltage converter; and a measuring circuit that measures voltage of one of the output ports through the PTC thermistor with respect to the reference potential and voltage of the other of the output ports with respect to the reference potential. In the aspect described above, the measuring circuit may output a signal that indicates the temperature abnormality when the absolute value of the voltage of one of the output ports through the PTC thermistor is different from the absolute value of the voltage of the other of the output ports. According to the aspect described above, the same effects as the first aspect described above can be provided.

Details of the technique disclosed herein and further modifications will be described in the following "DETAILED DESCRIPTION OF EMBODIMENTS".

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

A voltage measuring apparatus of an embodiment will be described with reference to the attached drawings. The voltage measuring apparatus of the embodiment is incorporated into a power conversion apparatus for an electric vehicle. An electrical system (drive system) of the electric vehicle is described first with reference to FIG. 1.

Figure 1:
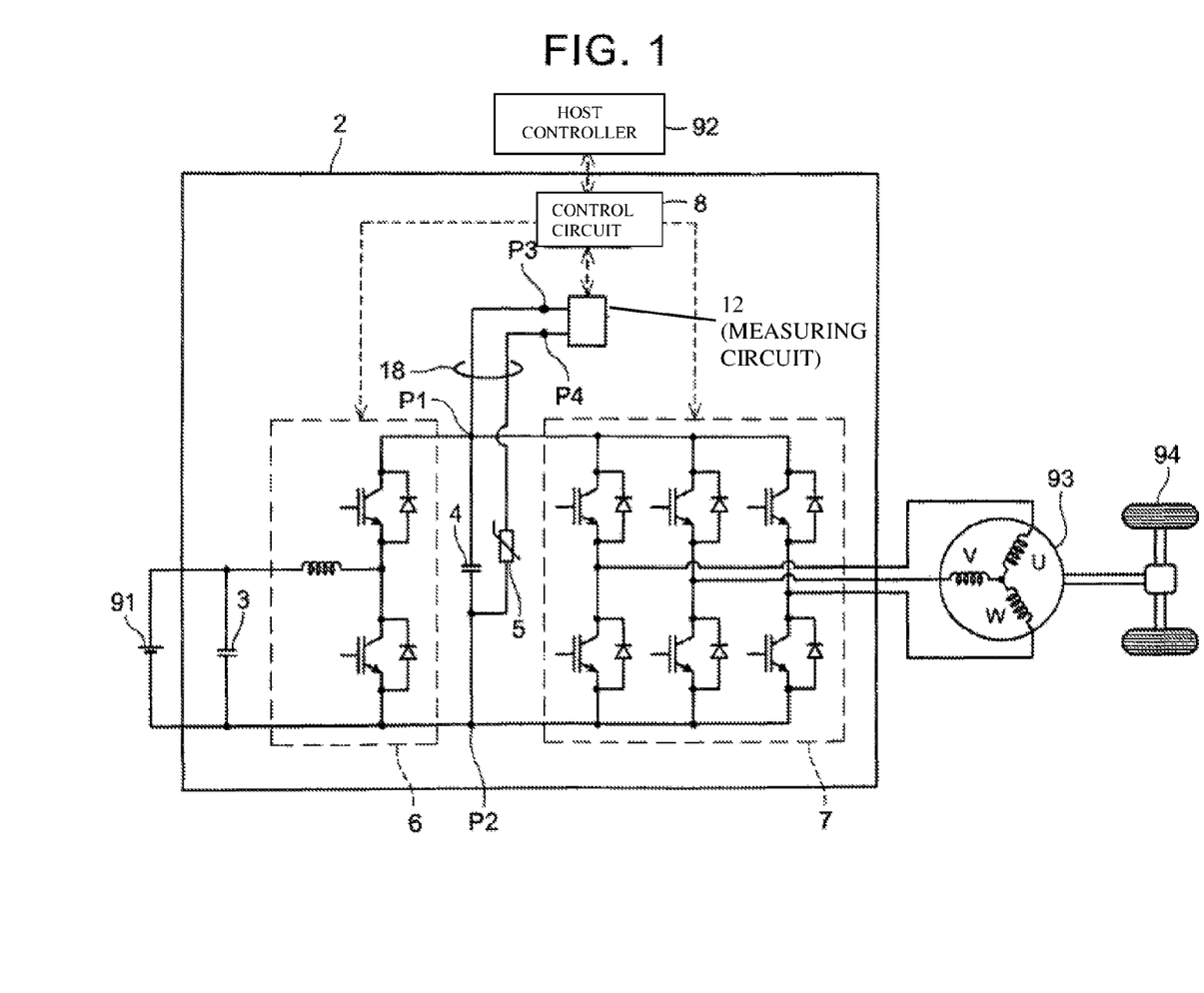
FIG. 1 is a block diagram that shows an electric power system of the electric vehicle.

A power conversion apparatus 2 boosts output voltage of a battery 91 and then converts it into alternating-current voltage. Hence, the power conversion apparatus 2 includes a voltage converter 6 and an inverter 7. The voltage converter 6 is provided with two transistors, two diodes, and a reactor to constitute a circuit shown in FIG. 1. The circuit structure of the voltage converter 6 shown in FIG. 1 is well known in the art, and thus the detailed description is not made.

A capacitor 3 is connected to an input side of the voltage converter 6 for smoothing the output current of the battery 91. A capacitor 4 is connected to an output side of the voltage converter 6, namely, the input side of the inverter 7 for smoothing the output current of the voltage converter 6. The power conversion apparatus 2 drives a drive motor and thus handles large current. Accordingly, the large current passes through the capacitors 3 and 4, and amounts of heat generation in the capacitors thus become large.

The output of the inverter 7 is supplied to the motor 93. Output torque of the motor 93 is transmitted to a driving wheel 94 through a differential gear. The output (power output) of the motor 93 corresponds to the output of the power conversion apparatus 2 and depends on vehicle speed or an accelerator operation amount. A host controller 92 for the power conversion apparatus 2 determines target output of the motor 93 in accordance with the vehicle speed or the accelerator operation amount. The target output of the motor 93 is sent to a control circuit 8 inside the power conversion apparatus 2. The control circuit 8 determines a boosting ratio of battery voltage or output frequency of the inverter required for obtaining the target output of the motor 93 and generates a switching element control signal, namely, a pulse width modulation (PWM) signal in response to the ratio or the frequency. The generated PWM signal is supplied to the voltage converter 6 or the inverter 7. It should be noted that small dashed lines with arrows shown in FIG. 1 (and FIG. 2) indicate the flow of signals.

The output voltage of the voltage converter 6 is described hereinafter. The drive motor 93 operates on the AC power that possesses a reference potential (ground potential) as zero potential and alternates between a positive potential and a negative potential with a specified voltage width as well known in the art. In other words, the output of the inverter 7 is the AC power that is converted with the reference potential as zero potential and the specified voltage width in the positive and the negative directions. Thus, an intermediate potential between a power-supply line on a high potential side and a power-supply line on a low potential side is set as the reference potential at the stage of direct current input into the inverter 7. More specifically, a terminal that possesses the intermediate potential between the high potential and the low potential in a power line is connected to the body of the vehicle (that is, a ground) at a stage prior to the inverter 7.

In the power conversion apparatus 2 of the embodiment, an input port of the inverter 7 and an input port and an output port of the voltage converter 6 possess the positive and the negative potential with the reference potential as zero. In other words, the voltage converter 6 (the input port of the inverter 7) maintains a positive output port at higher potential than the reference potential by half of target voltage and a negative output port at lower potential than the reference potential by the remaining half of the target voltage with respect to the target voltage of the voltage converter 6 that is determined in accordance with the target output of the motor 93. When the target voltage varies, the potential of the positive output port and the negative output port with respect to the reference potential each varies. In other words, the absolute value of the voltage of the positive output port with respect to the reference potential is equal to the absolute value of the voltage of the negative output port with respect to the reference potential. Even when the target voltage cannot be obtained, for example, in a case of the low state of charge (SOC) of the battery, the absolute value of the voltage of the positive output port with respect to the reference potential equals the absolute value of the voltage of the negative output port with respect to the reference potential. However, it should be noted that the discrepancy between the absolute value of the voltage of the positive output port with respect to the reference potential and the absolute value of the voltage of the negative output port with respect to the reference potential may arise within the range of error associated with voltage fluctuation or error caused by variations of circuit elements, for example. Thus, the absolute value of the voltage of the positive output port with respect to the reference potential and the absolute value of the voltage of the negative output port with respect to the reference potential are the same in the range that can accept specified variations.

The subject is now returned to the description of power conversion apparatus 2. A voltage measuring apparatus 10 measures the output voltage of the voltage converter 6 and detects the temperature abnormality of the capacitor 4. That is to say, the voltage measuring apparatus 10 outputs a signal that indicates the temperature abnormality when the temperature of the capacitor 4 is higher than a specified threshold temperature. The voltage measuring apparatus 10 includes a measuring circuit 12 and a thermistor 5. The thermistor 5 is of a positive temperature coefficient (PTC) type whose resistance sharply increases at a specified temperature or higher. The thermistor 5 is mounted on a location where the temperature is predicted to become the maximum, such as a lateral side of the element of the capacitor 4. More specifically, as described later with reference to FIG. 5, the capacitors 3 and 4 are packaged on one module, and the thermistor 5 is mounted on a location where the temperature tends to increase in the packaging. The thermistor 5 is selected from thermistors that have the Curie point temperature approximately equal to the upper limit temperature in the normal temperature range of the capacitor 4. The Curie point temperature is a temperature at which or higher the resistance sharply increases. The voltage measuring apparatus 10 outputs a signal that indicates the occurrence of the temperature abnormality of the capacitor when the temperature of the capacitor 4 exceeds the Curie point temperature and the resistance increases.

The capacitor 4 is connected between the positive output port P1 and the negative output port P2 of the voltage converter 6. The positive output port P1 of the voltage converter 6 is connected to a positive input port P3 of the measuring circuit 12. The negative output port P2 of the voltage converter 6 is connected to one end of the thermistor 5. The other end of the thermistor 5 is connected to a negative input port P4 of the measuring circuit 12. In other words, the thermistor 5 is connected between the negative output port P2 of the voltage converter 6 and the negative input port P4 of the measuring circuit 12. In the power conversion apparatus 2, the voltage converter 6 and the voltage measuring apparatus 10 (measuring circuit 12) that measures the output voltage of the voltage converter 6 and detects the temperature abnormality of the capacitor are connected with only two cables 18. The circuit structure of the measuring circuit 12 is described next.

Figure 2:
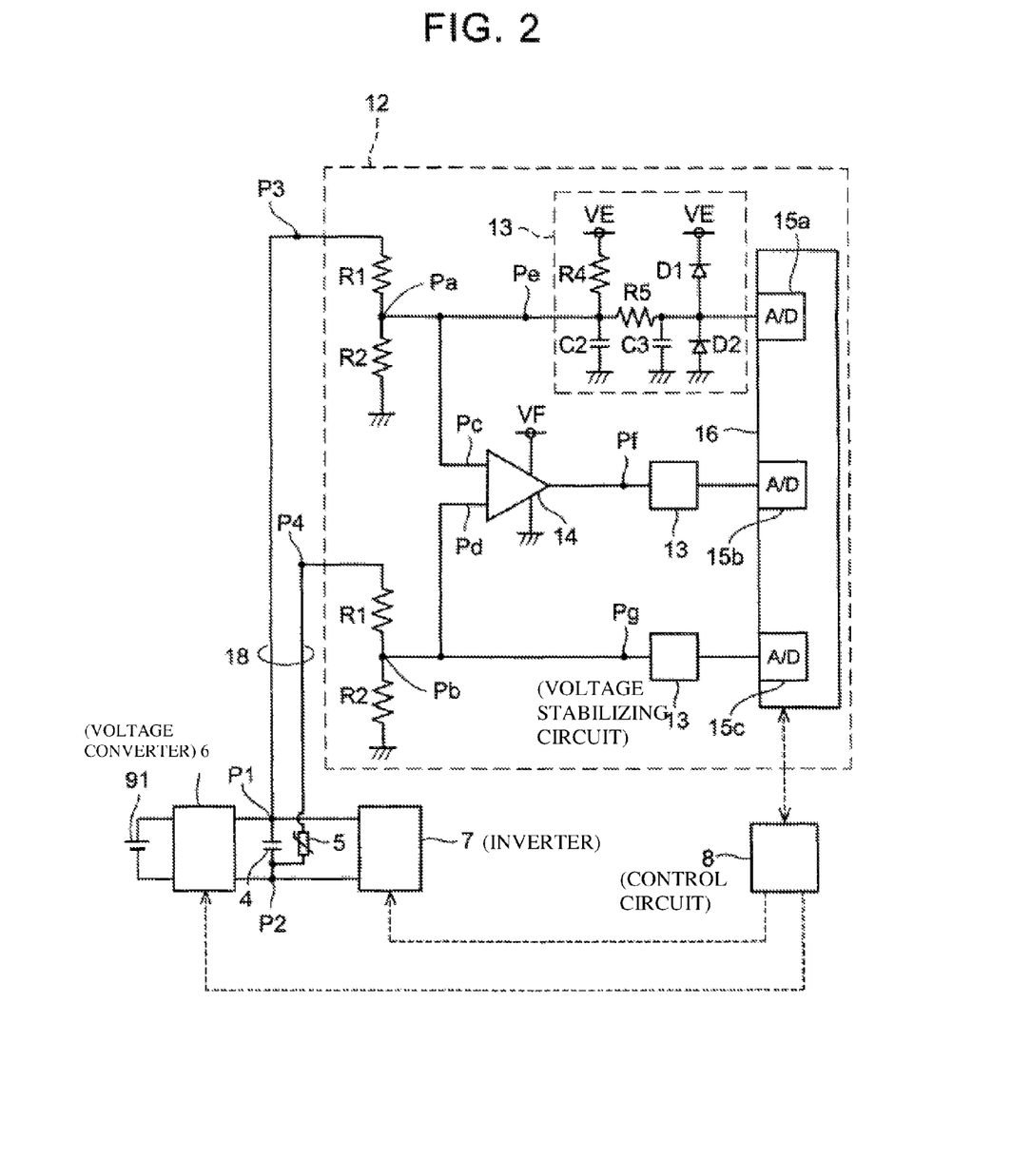
FIG. 2 is a circuit diagram of the voltage measuring apparatus.

FIG. 2 shows a circuit block diagram of the measuring circuit 12. A positive input port P3 is connected to resistors R1 and R2 in series. One terminal of the resistor R2 is connected to the ground (reference potential). The series connection circuit of the resistors R1 and R2 is a circuit that divides the voltage applied to the positive input port P3 and converts it into a low voltage. A 9.95 MΩ resistor is used for the resistor R1, and a 0.05 MΩ resistor is used for the resistor R2, for example. Then, the voltage at a midpoint Pa in the series connection of the resistors R1 and R2 becomes a value equal to the voltage applied to the positive input port P3 times R2/(R1+R2)(=0.005). For example, when 100 volts are applied to the positive input port P3, the voltage at the midpoint Pa becomes 0.5 volts. A negative input port P4 is similarly connected to the resistors R1 and R2 in series. The other terminal of the resistor R2 is connected to the ground. The divided voltage of the voltage applied to the negative input port is applied to a midpoint Pb between the resistors R1 and R2.

The voltages at the midpoints Pa and Pb have proportional relations with the voltages of the positive and the negative output ports of the voltage converter 6, respectively. As shown in FIG. 2, the voltages at the midpoints Pa and Pb indicate the voltages of the output ports of the voltage converter 6 with respect to the ground (reference potential). The measuring circuit 12 measures the voltages of the positive and the negative output ports of the voltage converter 6 with respect to the ground (reference potential).

The midpoint Pa is connected to a first analog-digital (A/D) input port 15a of a microcomputer chip 16 through a voltage stabilizing circuit 13. That is to say, the voltage of the positive output port P1 of the voltage converter 6 applied to the midpoint Pa is fed into the first A/D input port 15a of the microcomputer chip 16. The voltage stabilizing circuit 13 includes resistors R4 and R5, capacitors C2 and C3, and diodes D1 and D2 and has a structure shown in FIG. 2. The voltage stabilizing circuit 13 is well known in the art, and thus the detailed description thereof is not made. A reference symbol VE in the drawing denotes a power-supply line of the measuring circuit 12, and its voltage is 5 volts, for example.

The midpoint Pb is similarly connected to a third A/D input port 15c of the microcomputer chip 16 through the voltage stabilizing circuit 13. That is to say, the voltage of the negative output port P2 of the voltage converter 6 applied to the midpoint Pb is fed into the third A/D input port 15c of the microcomputer chip 16. However, it should be noted that the voltage fed into the third A/D input port 15c of the microcomputer chip 16 is the voltage of the negative output port P2 via the thermistor 5.

The midpoints Pa and Pb are connected to two input ports Pc and Pd of a differential amplifier 14. The differential amplifier 14 amplifies and outputs the difference between the voltage at the midpoint Pa and the voltage at the midpoint Pb. That is to say, the output of the differential amplifier 14 corresponds to a measured value of the voltage between the positive output port and the negative output port of the voltage converter 6. The output of the differential amplifier 14 is fed into a second A/D input port 15b of the microcomputer chip 16 through the voltage stabilizing circuit 13. A reference symbol VF in the drawing denotes a drive voltage source of the differential amplifier 14, and its voltage is 15 volts, for example.

The A/D input ports 15a, 15b, and 15c correspond to the input ports that digitize applied analog voltages and import them into the microcomputer chip 16 which is a digital controller.

As a result, three input ports Pe, Pf, and Pg of the microcomputer chip 16 are respectively fed with the voltage of the positive output port of the voltage converter 6 with respect to the ground (reference potential), the voltage difference between the positive output port and the negative output port of the voltage converter 6, and the voltage of the negative output port of the voltage converter 6 with respect to the ground. It is obvious that, in a precise sense, the voltage of the input port Pe is the voltage corresponding to "the voltage of the positive output port of the voltage converter 6 with respect to the ground"; however, the voltage of the input port Pe may substantially be considered as "the voltage of the positive output port of the voltage converter 6 with respect to the ground". Hereinafter, the measured value of the voltage of the positive output port P1 of the voltage converter 6 with respect to the ground is referred to as a "positive electrode measurement voltage", the measured value of the voltage difference between the positive output port P1 and the negative output port P2 of the voltage converter 6 is referred to as a "converter output measurement voltage", and the measured value of the voltage of the negative output port P2 of the voltage converter 6 with respect to the ground is referred to as a "negative electrode measurement voltage". The thermistor 5 exerts influence on the converter output measurement voltage and the negative electrode measurement voltage. However, when the temperature abnormality does not occur, the resistance of the thermistor 5 is small, and the converter output measurement voltage may be considered as the actual output voltage of the voltage converter 6.

The processing executed by the microcomputer chip 16 is described next. The microcomputer chip 16 cooperates with the voltage converter 6 and the control circuit 8 that controls the inverter 7 to monitor whether or not the output of the voltage converter 6 is approximately equal to the target voltage and whether or not the temperature of the capacitor 4 exceeds the normal temperature range. The case where the temperature of the capacitor 4 exceeds the normal temperature range corresponds to the temperature abnormality. In addition, the case where the output of the voltage converter 6 is not equal to the target voltage is referred to as a system voltage abnormality (system voltage error).

The potential of the output port of the voltage converter 6 is described again before the processing of the microcomputer chip 16 is described. As described above, relative to the target voltage of the voltage converter 6 that is determined by the control circuit 8, the potential (voltage) of the positive output port P1 with respect to the ground (reference potential) is [+target voltage/2], and the potential (voltage) of the negative output port P2 with respect to the ground is [−target voltage/2]. In other words, when the voltage converter 6 operates normally, it maintains the positive output port P1 at higher potential than the ground by half of target voltage and the negative output port P2 at lower potential than the ground by the remaining half of the target voltage. Even if the output of the voltage converter 6 does not reach the target voltage, the absolute value of the potential (voltage) of the positive output port P1 with respect to the ground is approximately equal to the absolute value of the potential (voltage) of the negative output port P2 with respect to the ground. For example, when the potential of the positive output port P1 with respect to the ground is +A, the potential of the negative output port P2 with respect to the ground becomes −A.

Figure 3:
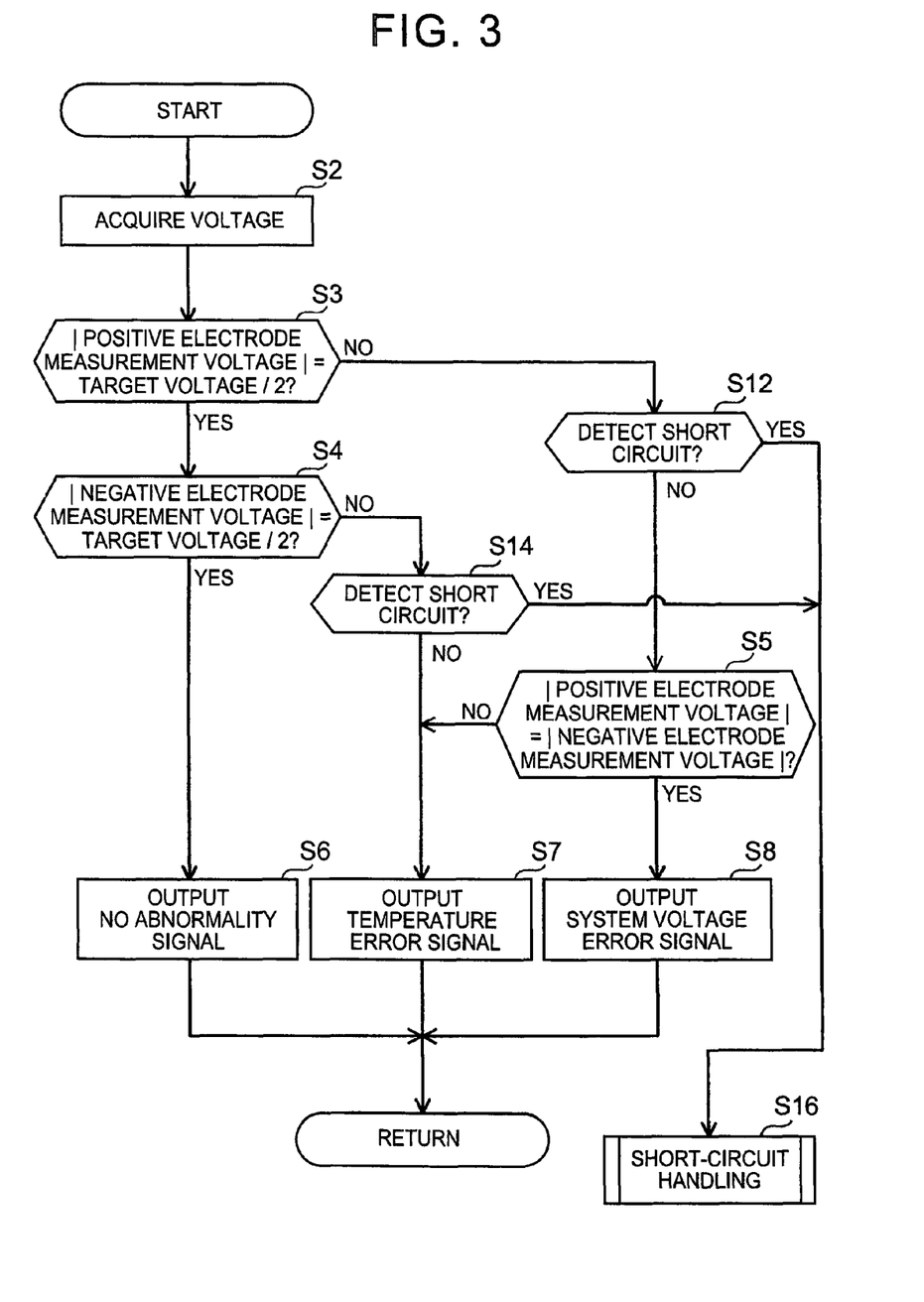
FIG. 3 is a flowchart that shows the processes of the temperature abnormality detection and/or the converter abnormality detection for the voltage measuring apparatus.

The processing executed by the microcomputer chip 16 (measuring circuit 12) is described with reference to FIG. 3. The processing of the flowchart in FIG. 3 is executed in each control period. The microcomputer chip 16 first acquires the voltages that are obtained at the first to the third A/D input ports 15a to 15c, namely, the positive electrode measurement voltage, the converter output measurement voltage, and the negative electrode measurement voltage (S2). The microcomputer chip 16 then determines whether or not the absolute value of the positive electrode measurement voltage is equal to the target voltage (S3). The microcomputer chip 16 communicates with the control circuit 8 that controls the voltage converter 6 and the inverter 7 and acquires the target voltage from the control circuit 8.

When the absolute value of the positive electrode measurement voltage is equal to the target voltage (S3: YES), the microcomputer chip 16 then determines whether or not the absolute value of the negative electrode measurement voltage is equal to the target voltage (S4). When the absolute value of the negative electrode measurement voltage is also equal to the target voltage, as the microcomputer chip 16 determines that the voltage converter 6 outputs the target voltage and the temperature abnormality of the capacitor 4 does not occur, the microcomputer chip 16 outputs a signal indicating that no abnormality is detected to the control circuit 8 (S6). Hereinafter, the "absolute value of the positive electrode measurement voltage" may simply be referred to as the "positive electrode measurement voltage", and also the "absolute value of the negative electrode measurement voltage" may simply be referred to as the "negative electrode measurement voltage". It should be noted that symbols expressing the absolute value are given in the flowchart of FIG. 3.

On the other hand, when the positive electrode measurement voltage is equal to the target voltage/2 (S3: YES) but the negative electrode measurement voltage is not equal to the target voltage/2 (S4: NO), it means that the positive output port P1 or the negative output port P2 shorts out or the resistance of the PTC thermistor 5 is large. The electric vehicle is generally equipped with a circuit for detecting the short circuits, and when the step S4 is determined as NO, the detecting circuit first verifies whether or not the system shorts out (S14). When the short circuit is not detected (S14: NO), it means that the temperature of the PTC thermistor 5, namely, the temperature of the capacitor 4 exceeds the specified threshold (Curie point temperature of the PTC thermistor 5). In this case, the microcomputer chip 16 outputs the signal indicating that the temperature abnormality occurs on the capacitor 4 (temperature error signal) to the control circuit 8 (S7). When the short circuit is detected in the step S14, the control is shifted from a temperature abnormality detection routine in FIG. 3 to a short-circuit handling routine (S16). The description of the short-circuit handling routine is not made here.

Meanwhile, in the step S3, when the positive electrode measurement voltage is not equal to the target voltage/2 (S3: NO), the microcomputer chip 16 verifies whether or not the short circuit is detected (S12) and then evaluates whether or not (the absolute value of) the positive electrode measurement voltage is equal to (the absolute value of) negative electrode measurement voltage (Step S5). When the both absolute values are not the same (Step S5: NO), the microcomputer chip 16 determines that the cause of inequality is the large resistance of the PTC thermistor 5 and then outputs the signal indicating that the temperature abnormality occurs (temperature error signal) to the control circuit 8 (Step S7). On the other hand, when the both absolute values are the same in the step S5, it means that the temperature abnormality does not occur but the output voltage of the voltage converter 6 does not reach the target voltage, and thus the microcomputer chip 16 sends the signal indicating that some kind of abnormality occurs on the voltage converter 6 (system voltage error signal) to the control circuit 8 (Step S8). In this case, the causes are supposed in which the output voltage of the voltage converter 6 does not reach the target voltage because of the low state of charge of the battery, for example. Or, in this case, system errors can be supposed in which the voltage abruptly fluctuates due to overspeed of the motor, for example.

The temperature error signal is transmitted from the control circuit 8 to the host controller 92 (see FIG. 1). The host controller 92 that receives the temperature error signal displays a warning that shows the error on an instrument panel of the vehicle or applies limitations on the target output of the motor 93, for example. When a converter abnormality occurs, the system voltage error signal is transmitted from the control circuit 8 to the host controller 92. The host controller 92 that receives the system voltage error signal executes preprogrammed handling processes such as displaying a warning that shows the error on the instrument panel of the vehicle, for example.

Figure 4:
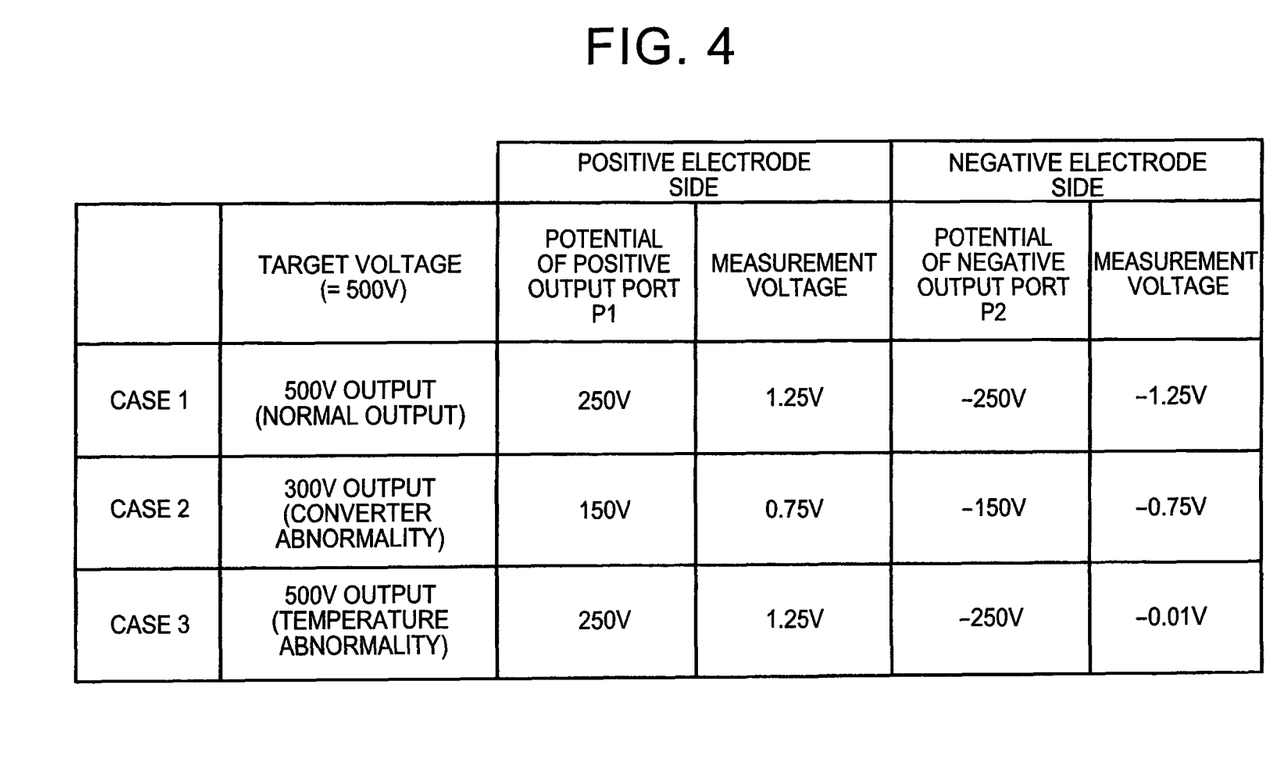
FIG. 4 is a table that shows one example of voltage measurement values in the cases of the occurrences of a normal state, the converter abnormality, and the temperature abnormality.

Specific examples of a case where the temperature abnormality occurs on the voltage converter, a case where the converter abnormality occurs, and a case where no abnormality occurs are described below with numerical examples. FIG. 4 shows the numerical examples. In this example, the target voltage is set to 500 volts, and the resistors R1 and R2 in FIG. 2 are assumed to be 9.95 MΩ and 0.05 MΩ, respectively.

When the voltage converter 6 normally operates (that is, the output is equal to the target voltage) and the temperature abnormality does not occur (Case 1), the potentials of the positive output port P1 and the negative output port P2 of the voltage converter 6 with respect to the ground are +250 volts and −250 volts, respectively. The measurement voltages in the measuring circuit at this time are +1.25 volts and −1.25 volts, respectively. In other words, both of the absolute value of the positive electrode measurement voltage and the absolute value of the negative electrode measurement voltage are equal to half of the target voltage. In this case, the processing of the steps S3, S4, and S6 in the flowchart of FIG. 3 is executed.

When the temperature abnormality does not occur, but some kind of abnormality occurs on the voltage converter 6, and thus the output voltage does not reach the target voltage (500 volts) but is 300 volts, the potentials of the positive output port P1 and the negative output port P2 with respect to the ground are +150 volts and −150 volts, respectively. The measurement voltages in the measuring circuit at this time are +0.75 volts and −0.75 volts, respectively. In other words, the absolute value of the positive electrode measurement voltage and the absolute value of the negative electrode measurement voltage are the same but not equal to half of the target voltage. In this case, the processing of the steps S3, S5, and S8 in the flowchart of FIG. 3 is executed.

When the voltage converter normally operates but the temperature abnormality occurs, the potentials (voltages) of the positive output port P1 and the negative output port P2 with respect to the ground are +250 volts and −250 volts, respectively. However, the measurement voltages in the measuring circuit are +1.25 volts and −0.01 volts, respectively. In other words, the absolute value of the positive electrode measurement voltage is equal to half of the target voltage, but the absolute value of the positive electrode measurement voltage is not equal to the absolute value of the negative electrode measurement voltage. In this case, the processing of the steps S3, S4, and S7 in the flowchart of FIG. 3 is executed.

As described above, the voltage measuring apparatus 10 of the embodiment can measure the voltage between the output ports and detect the temperature abnormality with only the two cables 18 that are connected to the voltage converter 6. This apparatus has an advantage that a cable dedicated to the temperature abnormality detection is not required. As shown in FIG. 2, the measuring circuit 12 that measures the output voltage of the voltage converter 6 detects the temperature abnormality. In other words, the voltage measuring apparatus 10 of the embodiment has the advantage that a circuit dedicated to detecting the temperature abnormality is not required since the circuit for voltage measurement can also detect the temperature abnormality.

Figure 5:
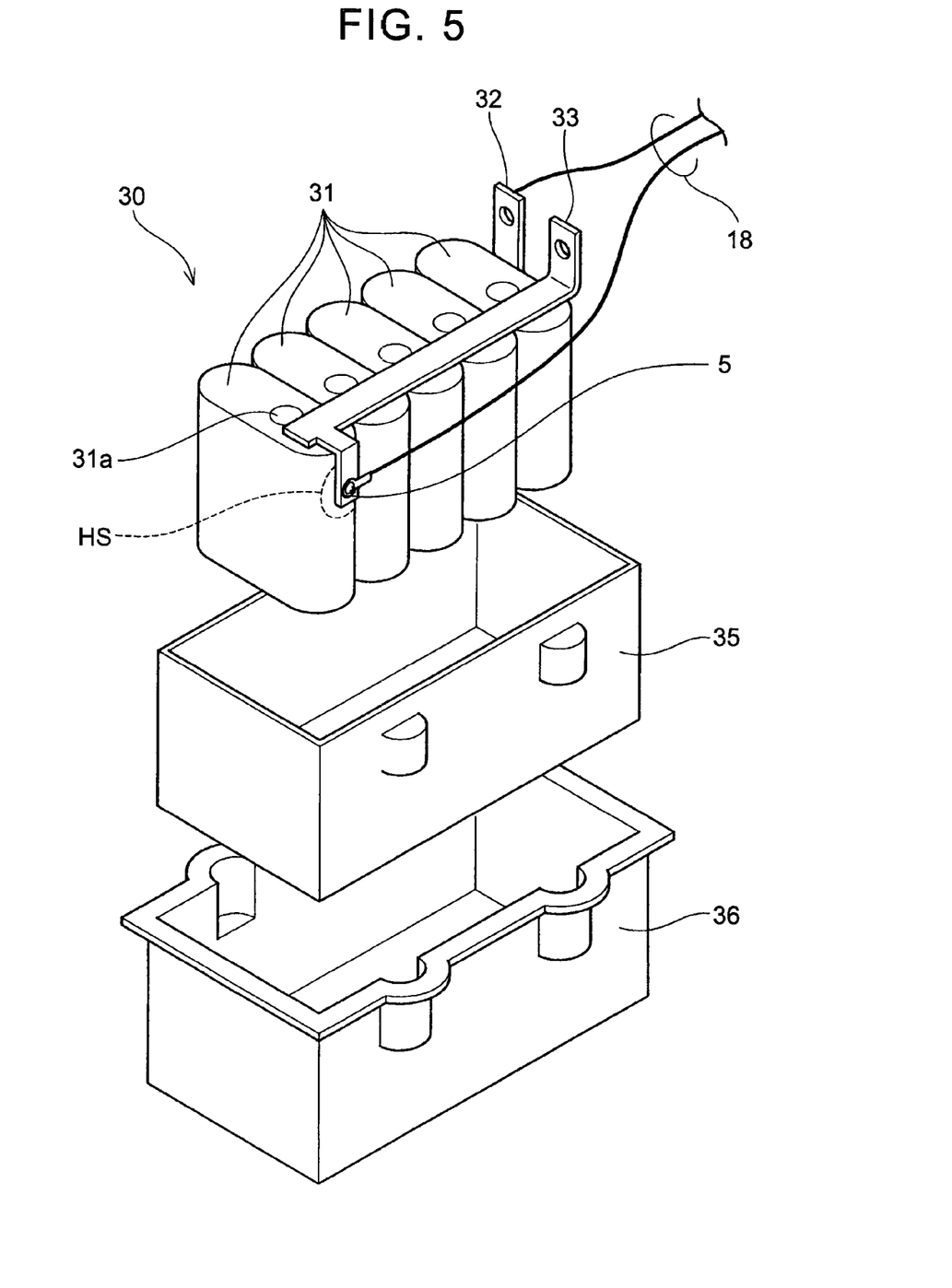
FIG. 5 is a diagram that shows one example of thermistor mounting.

A mounting example of the thermistor 5 is described next. FIG. 5 shows an exploded perspective view of a capacitor module 30. The actual device of the capacitor 4 on the circuit diagram shown in FIG. 1 or FIG. 2 is a plurality of capacitor elements 31 that are connected in parallel. Capacitance is increased by connecting the plurality of capacitor elements 31 in parallel. The plurality of capacitor elements 31 are arranged in parallel, and a bus bar 33 is mounted so as to come into contact with all negative terminals 31a. Not illustrated in FIG. 5, positive terminals are exposed in the bottom surface of the capacitor elements 31, and a bus bar 32 is mounted so as to come into contact with all positive terminals. The bus bar 32 is a conductive member that connects the positive terminals of the capacitor elements 31 (capacitor 4 in FIGS. 1 and 2) to the positive output port of the voltage converter 6, and the bus bar 33 is a conductive member that connects the negative terminals of the capacitor elements 31 (capacitor 4 in FIGS. 1 and 2) to the negative output port of the voltage converter 6. The bus bars 32 and 33 respectively correspond to the positive output port and the negative output port of the voltage converter 6.

A part of the bus bar 33 for the negative electrode extends to a lateral side of one of the capacitor elements 31, and the thermistor 5 is mounted in the end by means of a screw. A surface region HS of the capacitor corresponding to the mounting position is a region where the temperature is expected to become highest in the set of the plurality of the capacitor elements 31. The thermistor 5 is fixed to the bus bar 33 for the negative electrode with the screw and conducts electricity. The cable that is connected to the measuring circuit 12 of the voltage measuring apparatus 10 extends from the end of the thermistor 5. A cable that is connected to the measuring circuit 12 extends to the bus bar 32 for the positive electrode. Two cables 18 shown in FIG. 5 are cables that connect the positive output port and the negative output port of the voltage converter 6 to the measuring circuit 12 of the voltage measuring apparatus 10. The voltage measuring apparatus 10 can execute two functions of measuring the voltage and detecting the temperature abnormality of the capacitor by using the voltage values applied in each of the two cables 18.

The plurality of capacitor elements 31 that are bundled in line are housed in an inner case 35. Then, the inner case 35 is housed in an outer case 36. It should be noted that the mounting position of the thermistor shown in FIG. 5 is one example. The thermistor 5 is mounted at a position where the temperature is expected to become highest. When the temperature abnormality over a large area is required to be detected, it is preferable that target area be covered with a sheet having high thermal conductivity and the thermistor be mounted on the sheet.

Considerations about the technique described in the embodiment will be described. The voltage measuring apparatus 10 of the embodiment is incorporated into the power conversion apparatus 2, measures the voltage between the output ports of the voltage converter 6, and monitors the temperature abnormality of the capacitor 4 connected to the output ports in parallel. As clearly seen from FIG. 1 and FIG. 2, the output port of the voltage converter 6 corresponds to the input port of the inverter 7. Consequently, the voltage measuring apparatus 10 of the embodiment can be described as follows. That is to say, the voltage measuring apparatus 10 measures the voltage between the direct-current input ports P1 and P2 of the inverter 7 and detects the abnormality on the capacitor 4 connected to the direct-current input ports in parallel.

The voltage measuring apparatus 10 disclosed herein can also practically be used as an apparatus that measures the voltage between the output ports of the battery 91 and detects the abnormality of the capacitor 3 connected to the output ports in parallel. When used as such an apparatus, the voltage measuring apparatus 10 may be connected across the terminals of the capacitor 3.

The subject of the temperature abnormality detection is not limited to the capacitors. For example, the subject of the temperature abnormality detection may be switching elements in the voltage converter and the inverter. The embodiment described above is one in which the technique disclosed herein is applied to the power conversion apparatus 2 for the electric vehicle. More specifically, the embodiment is an apparatus that measures the voltage of the output port of the voltage converter in the power conversion apparatus and detects the temperature abnormality of a current smoothing capacitor connected to the output port. The structure of the power conversion apparatus can be summarized as follows. The power conversion apparatus 2 is a device that boosts the electric power of the battery 91 and then converts it into alternating-current power for driving the drive motor (motor 93). The power conversion apparatus 2 includes the voltage converter 6 that boosts the output voltage of the battery 91, the capacitor 4, the PTC thermistor 5, and the control circuit 8. The voltage converter 6 maintains the positive output port P1 at higher potential than the reference potential and the negative output port P2 at lower potential than the reference potential. As described above, the reference potential corresponds to the zero potential of the alternating-current power supplied to the motor. The capacitor 4 is connected between the output ports (between the positive output port P1 and the negative output port P2) of the voltage converter 6. The PTC thermistor 5 is mounted on the capacitor 4 and connected to one of the output ports (for example, negative output port P2) of the voltage converter 6. The measuring circuit 12 measures the voltage of one of the output ports (negative output port P2) through the PTC thermistor with respect to the reference potential and the voltage of the other of the output ports (for example, positive output port P1) with respect to the reference potential. The measuring circuit 12 outputs the signal indicating the temperature abnormality detection when the absolute value of the voltage of one of the output ports (negative output port P2) through the PTC thermistor is different from the absolute value of the voltage of the other of the output ports (positive output port P1). It should be noted that, in the above description, the positions of the positive output port P1 and the negative output port P2 may be inverse.

While the present invention has been described in detail with reference to example embodiments thereof, it is to be understood that those examples are merely illustrative and claims of the present invention are not limited to those examples. The techniques that are disclosed in the claims of the present invention are intended to cover various modifications and changes of the example embodiments that are described above. In addition, the technical elements that are disclosed in the specification and the drawings exhibit technical usefulness alone or in various combinations and configurations, and those are not limited to the combinations and configurations that are disclosed in the claims at the time of filing this application. The techniques that are illustrated in the specification and the drawings can achieve a plurality of objects simultaneously, and the achievement of one object thereof itself has technical usefulness.

The invention claimed is:

1. A voltage measuring apparatus for measuring voltage between a positive terminal and a negative terminal of a device,
    the voltage measuring apparatus comprising:
        a PTC thermistor mounted on a location, of the device or components associated with the device, where temperature is predicted to become maximum; and
        a measuring circuit including a first terminal and a second terminal respectively connected to the device, the PTC thermistor being connected to the first terminal in series, and the measuring circuit being configured to measure voltage of the first terminal with respect to a specified reference potential and voltage of the second terminal with respect to the reference potential,
    wherein the voltage measuring apparatus is configured to output a signal that indicates temperature abnormality when an absolute value of the voltage of the first terminal is different from an absolute value of the voltage of the second terminal.

2. The voltage measuring apparatus according to claim 1, wherein the device is a voltage converter configured to maintain the positive terminal at higher potential than the reference potential and the negative terminal at lower potential than the reference potential.

3. The voltage measuring apparatus according to claim 1, wherein the device is an inverter configured to supply electric power to a drive motor for an electric vehicle, the voltage measuring apparatus is connected to direct-current input ports of the inverter, the potential of a positive electrode in the direct-current input ports of the inverter is maintained at higher potential than the reference potential, and the potential of a negative electrode in the direct-current input ports is maintained at lower potential than the reference potential.

4. The voltage measuring apparatus according to claim 1, wherein the PTC thermistor is mounted on a capacitor that is connected between the positive terminal and the negative terminal of the device.

5. The voltage measuring apparatus according to claim 4, wherein the voltage measuring apparatus is incorporated into a power conversion apparatus for an electric vehicle that converts output power of a battery into alternating-current power for driving a drive motor.

6. A power conversion apparatus for boosting electric power of a battery and then converting the electric power into alternating-current power for driving a drive motor, the power conversion apparatus comprising:
    a voltage converter configured to boost output voltage of the battery, the voltage converter being configured to maintain a positive output port at higher potential than reference potential corresponding to zero potential of the alternating-current power and a negative output port at lower potential than the reference potential;
    a capacitor connected between the positive output port and the negative output port of the voltage converter;
    a PTC thermistor mounted on the capacitor; and
    a measuring circuit including a first terminal and a second terminal respectively connected to the voltage converter, the PTC thermistor being connected to the first terminal in series, the measuring circuit being configured to measure voltage of the first terminal with respect to the reference potential and voltage of the second terminal with respect to the reference potential, the first terminal being connected to either the positive output port or the negative output port, and the second terminal being connected the other of the negative output port or the positive output port,
    wherein the measuring circuit is configured to output a signal that indicates temperature abnormality when an absolute value of the voltage of the first terminal is different from an absolute value of the voltage of the second terminal.

* * * * *